US012105168B2

(12) United States Patent
Biber et al.

(10) Patent No.: US 12,105,168 B2
(45) Date of Patent: Oct. 1, 2024

(54) OPERATING AN MRI APPARATUS

(71) Applicant: Siemens Healthcare GmbH, Erlangen (DE)

(72) Inventors: Stephan Biber, Erlangen (DE); Adrian Bampton, Abingdon (GB); Markus Vester, Nuremberg (DE); Andre de Oliveira, Uttenreuth (DE); Volker Model, Fürth (DE); Jürgen Nistler, Erlangen (DE); Andreas Potthast, Erlangen (DE); Adam Paul Johnstone, Thame (GB)

(73) Assignee: Siemens Healthineers AG, Forchheim (DE)

( * ) Notice: Subject to any disclaimer, the term of this patent is extended or adjusted under 35 U.S.C. 154(b) by 68 days.

(21) Appl. No.: 17/882,526

(22) Filed: Aug. 5, 2022

(65) Prior Publication Data

US 2022/0381860 A1 Dec. 1, 2022

Related U.S. Application Data

(60) Continuation of application No. 17/386,533, filed on Jul. 27, 2021, now Pat. No. 11,550,009, which is a (Continued)

(51) Int. Cl.
*G01V 3/00* (2006.01)
*A61B 5/055* (2006.01)
(Continued)

(52) U.S. Cl.
CPC .......... *G01R 33/3815* (2013.01); *A61B 5/055* (2013.01); *G01R 33/446* (2013.01); *G01R 33/3635* (2013.01); *G01R 33/54* (2013.01)

(58) Field of Classification Search
CPC ....................................................... A61G 1/02
(Continued)

(56) References Cited

U.S. PATENT DOCUMENTS 5,769,778 A * 6/1998 Abrams .................. A61N 2/006
128/897
5,786,695 A * 7/1998 Amor .................. G01R 33/3873
324/319

(Continued)

FOREIGN PATENT DOCUMENTS

CN 103969610 A 8/2014
CN 104224179 A 12/2014
(Continued)

OTHER PUBLICATIONS

Parkinson, Ben. "Design considerations and experimental results for MRI systems using HTS magnets." Superconductor Science and Technology 30.1 (2016): 014009.

*Primary Examiner* — Walter L Lindsay, Jr.
*Assistant Examiner* — Frederick Wenderoth
(74) *Attorney, Agent, or Firm* — Lempia Summerfield Katz LLC

(57) ABSTRACT

A method of operating a magnetic resonance imaging (MRI) apparatus includes exciting a body coil of the MRI apparatus to emit a radio-frequency signal, determining a center frequency of a resonance curve of the body coil, and calculating a magnet target frequency based on the determined center frequency. A magnet is ramped to the magnet target frequency.

19 Claims, 8 Drawing Sheets

Related U.S. Application Data division of application No. 16/546,296, filed on Aug. 20, 2019, now Pat. No. 11,193,997.

(51) Int. Cl.
*G01R 33/3815* (2006.01)
*G01R 33/44* (2006.01)
*G01R 33/36* (2006.01)
*G01R 33/54* (2006.01)

(58) Field of Classification Search
USPC .......................................... 324/318
See application file for complete search history.

(56) References Cited

U.S. PATENT DOCUMENTS

| | | | |
|---|---|---|---|
| 8,271,067 B1 * | 9/2012 | Balakrishnan | G01R 33/546 |
| | | | 600/407 |
| 2002/0171520 A1 | 11/2002 | Yoshikawa | |
| 2005/0111159 A1 | 5/2005 | Knight | |
| 2012/0126813 A1 | 5/2012 | Paul | |
| 2014/0218021 A1 | 8/2014 | Koehler et al. | |
| 2014/0287602 A1 * | 9/2014 | Pons Gonzalez | H01R 13/6205 |
| | | | 439/39 |
| 2015/0301135 A1 | 10/2015 | Biber et al. | |
| 2017/0076043 A1 * | 3/2017 | Dormer | G16H 40/67 |
| 2018/0172787 A1 | 6/2018 | Aley et al. | |
| 2019/0072627 A1 | 3/2019 | Stainsby | |
| 2019/0107591 A1 | 4/2019 | Aley | |
| 2021/0018581 A1 | 1/2021 | Stainsby et al. | |

FOREIGN PATENT DOCUMENTS

| | | |
|---|---|---|
| CN | 105044636 A | 11/2015 |
| EP | 3614163 A1 | 2/2020 |
| JP | H0690918 A | 4/1994 |
| JP | 11087129 A * | 3/1999 |
| JP | H11164820 A | 6/1999 |
| JP | 2000147082 A * | 5/2000 |
| WO | 2017203330 A1 | 11/2017 |

* cited by examiner

OPERATING AN MRI APPARATUS

This application is a continuation patent application of U.S. patent application Ser. No. 17/386,533, filed on Jul. 27, 2021, which is a divisional patent application of U.S. patent application Ser. No. 16/546,296, filed on Aug. 20, 2019, which claims the benefit of European Patent Application No. EP 18189940.2, filed on Aug. 21, 2018, European Patent Application No. EP 18189973.3, filed on Aug. 21, 2018, and European Patent Application No. EP 18189964.2, filed on Aug. 21, 2018, which are hereby incorporated by reference in their entirety.

BACKGROUND

The present embodiments relate to operating a magnetic resonance imaging (MRI) apparatus.

Developments in the field of MRI systems have led to advances in low-field systems, which may be preferred on account of a smaller footprint. Low-field systems may be open-bore, may allow interventional procedures, and are less expensive. The term "low-field system" generally refers to a system that has a magnetic field strength of at most 1.0 Tesla. An MRI system with a magnetic field strength in excess of 1.0 Tesla is generally referred to as a "high-field system." The magnetic field strength of the low-field systems currently in development may be even lower than 1.0 Tesla, and may even be lower than 0.5 Tesla.

When an MRI system is first installed on site, a ramping procedure is carried out to set up the main magnetic field (also referred to as the static background field) in the main coil windings. After the initial installation ramping procedure, shim coils are used to perform any adjustments necessary to take into account the local environment. Usually, the target frequency (e.g., the center frequency of the main magnet) is determined with the aid of a probe placed at a suitable position in the apparatus. To allow for the inevitable decay of the magnetic field arising from component aging, typically in the order of several hundred ppm per year, this target frequency generally exceeds the center frequency of the body coil by an amount that is sufficient to provide that the center frequency of the main magnetic field remains above the body coil center frequency for as long as possible.

In any superconducting MRI system, decay of the magnetic field is unavoidable due to the residual electrical resistance of the magnet. Field decay provides that the center frequency of the main magnetic field gradually drifts away from the initial setting. Ultimately, it becomes necessary to re-ramp the system. In a high-field system, the bandwidth of the body coil and radio-frequency system is so large (e.g., body coil bandwidth ±100 kHz or more) that it may take several years before field decay is out of specification. Generally, another service procedure such as a cold head exchange is to be scheduled sooner. To carry out such a service procedure, the magnet is to be ramped down and up, so an opportunity is given to re-calibrate the system.

Before ramping the magnet, a target frequency for the main magnetic field is identified. It is usual to set the highest possible target frequency and to use the shim coils for any fine-tuning of the main magnetic field. By setting the highest possible target frequency, the decay window (e.g., the time taken for the frequency to drift to the lower end of the allowed band) is made as long as possible. This approach is suitable for systems with a high bandwidth, as explained above. However, the bandwidth of a low-field system is significantly narrower than that of a high-field system, being only on the order of 10 kHz-25 kHz, so that prior art methods of setting the magnet target frequency are limited to a much shorter "decay window." Because the decay window is narrower, the magnet frequency of a low-field MRI system decays towards an out-of-spec level in a shorter space of time. This provides that low-field MRI systems are generally to be ramped more often.

The first superconducting low-field MRI systems were generally configured as vertical field systems, characterized by a relatively inefficient body coil. These early low-field vertical systems are known to be less reliable than a comparable horizontal field system (e.g., with a birdcage body coil), so that service checks are to be scheduled relatively frequently. During these service procedures, the frequency of the main magnetic field is checked and the system is re-ramped if necessary. In a low-field system, it may be necessary to carry out an intermittent ramping procedure (e.g., in the event of an infrastructure problem such as a loss of power or problems with a cooling issues arrangement, etc.).

Ideally, the center frequency of the body coil would be the same as the frequency of the main magnet field. However, with a low-field magnet, reflection effects reduce the accuracy of the system, and the center frequency is lower.

The narrow bandwidth of the radio-frequency system, especially the body coil and the receiver coils, provides that reflection coefficients significantly reduce the available power from the radio frequency power amplifier (RFPA). When the reflection coefficients from the body coil are not equal, power is partly reflected back into the RFPA, which leads to a derating of the RFPA. This reduces the available power for the radio frequency magnetic field generated by the transmit coil or body coil. This magnetic field is generally referred to as the B1 field. Furthermore, the center frequency of the magnet and the center frequency of the body coil are not necessarily identical. For these reasons, the magnet center frequency is to be greater than the body coil center frequency to allow for inevitable main magnet field decay over time. However, it is difficult to identify a magnet target frequency that works satisfactorily within the constraints of narrow body coil bandwidth and high reflection coefficients.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a way of ramping a magnetic resonance imaging (MRI) apparatus that overcomes problems outlined above is provided.

According to an embodiment, a method of operating an MRI apparatus includes exciting a body coil of the MRI apparatus to emit a radio-frequency signal, determining a center frequency of a reflected radio-frequency signal, calculating a magnet target frequency based on the determined center frequency, and ramping a magnet to the magnet target frequency.

The magnet is ramped at a scheduled time, where this may be that the magnet field is monitored continually during operation of the MRI apparatus. When it is detected that the magnet field has decayed to a level approaching a lower limit, an alert may be issued to an operator who may then schedule a ramp procedure at a next convenient opportunity.

An advantage of one or more of the present embodiments is that the center frequency of the body coil resonance curve is empirically determined and used as a basis for computing the magnet target frequency. This is advantageous in, for example, low-field systems for which the body coil bandwidth is relatively narrow. A further advantage is that very little additional effort is required to implement the method of one or more of the present embodiments. Instead of providing a way to tune the body coil and another way to tune the magnet, one or more of the present embodiments take the approach of using the body coil as it is, and tuning the magnet based on the body coil. Any drift of the body coil center frequency (e.g., as a result of aging, from varying mechanical load on the patient table of the body coil, etc.) will be taken into consideration in the target frequency for the magnet. In other words, the magnet will always be ramped to suit the momentary state of the body coil. The body coil will be tuned to within a specified frequency bandwidth.

According to one or more of the present embodiments, the MRI apparatus includes a body coil excitation unit for exciting a body coil to emit a radio-frequency signal. The MRI apparatus also includes a computation module (e.g., a processor) configured to determine the center frequency of the radio-frequency signal emitted by the body coil, a target frequency determination unit (e.g., the processor or another processor) configured to calculate a magnet target frequency based on the determined center frequency, and a ramp control unit (e.g., the processor, the other processor, or yet another processor) configured to initiate a ramping procedure to ramp the magnet to the target frequency.

Another advantage of the MRI apparatus of one or more of the present embodiments is that the MRI apparatus may be significantly more economical to run than a comparable prior art MRI apparatus, since a time interval between consecutive ramping events may be extended, resulting in less downtime (e.g., during which MRI scans cannot be performed).

According to one or more of the present embodiments, the method of operating an MRI apparatus includes identifying a first magnet target frequency based on a first tolerance window and identifying a second magnet target frequency based on a second tolerance window. The second tolerance window exceeds the first tolerance window. The method also includes selecting one of the magnet target frequencies, and, at a scheduled time, ramping the magnet of the MRI apparatus to the selected magnet target frequency.

A target frequency for a ramping procedure is constrained by the upper boundary of the tolerance window defined by the bandwidth of the radio-frequency system as explained above. In the context of one or more of the present embodiments, the first tolerance window has a different bandwidth than the second tolerance window (e.g., one tolerance window is narrower than the other). The two possible target frequencies will therefore also be different. Depending on the nature of the scheduled ramping procedure, the more appropriate of the two target frequencies is selected and used during the ramping procedure.

It may be assumed that the tolerance windows differ significantly (e.g., that the width of the first tolerance windows differs from the width of the second tolerance window by a significant amount; by at least 10 kHz-100 kHz).

According to one or more of the present embodiments, the MRI apparatus includes a first frequency determination device (e.g., a processor) for identifying a first magnet target frequency based on a first tolerance window, and a second frequency determination device (e.g., the processor or another processor) for identifying a second magnet target frequency based on a second tolerance window, whereby the second tolerance window exceeds the first tolerance window. The apparatus further includes a selection unit (e.g., the processor or another processor) configured to select one of the magnet target frequencies as appropriate. A ramp controller initiates a ramping procedure to ramp the magnet to the selected magnet target frequency.

An advantage of the MRI apparatus of one or more of the present embodiments is that the MRI apparatus may be significantly more economical to run, since the time interval between consecutive ramping events may be extended, resulting in less downtime (e.g., during which MRI scans cannot be performed).

As another example, a way of monitoring decay of the main magnetic field of an MRI apparatus is provided.

According to one or more of the present embodiments, the method of operating an MRI apparatus includes identifying a center frequency during successive imaging procedures (e.g., during patient scans) and recording each center frequency, and analyzing the center frequencies to identify a number of decay-related characteristics of the main magnetic field (e.g., the B0 field).

An advantage of one or more of the present embodiments is that the main magnetic field may be monitored during normal operation of the MRI apparatus without the need for any dedicated measuring devices or additional components. One or more of the present embodiments are based on the insight that the signal frequency detected at the receiver coil is related to the main magnetic field by the gyromagnetic ratio, and that the signal detected by the receiver coil may be used to deduce information relating to the temporal development of the magnetic field during successive scans. The field monitoring of the method is advantageous in, for example, low-field systems, in which the magnet field decay is to be remedied more frequently than an high-field systems. Very little additional effort is required to implement the method of one or more of the present embodiments, and essentially, all acts may be carried out by suitable algorithms that process signals that are observed in any case during normal operation of the MRI apparatus.

An advantage of one or more of the present embodiments is that a decay-related characteristic of the main magnetic field is derived entirely from measurements collected during patient scans (e.g., using measurements that are made in any case). No dedicated test measurements are to be made. The measurements may be collected while adjusting the frequency of the receive system at the beginning of a patient scan, for example. Alternatively or in addition, measurements may be collected at a point during the actual imaging sequence. In either case, the signal for which the center frequency is determined originates from the patient.

According to one or more of the present embodiments, the MRI apparatus includes a center frequency identifier module configured to identify a center frequency during an imaging procedure. The MRI apparatus also includes a storage module configured to record center frequencies identified during successive imaging procedures, and an analysis module configured to identify a number of decay-related characteristics of the main magnetic field from analysis of the recorded center frequencies.

At least some of the units or modules of the MRI apparatus mentioned above and below (e.g., the frequency determination unit and the selection unit) may be completely or partially configured as software modules running on a processor of a control unit of an MRI apparatus. A configuration largely in the form of software modules may have the advantage that applications already installed on an existing MRI system may be updated, with relatively little effort, to carry out the method acts of one or more of the present embodiments.

As yet another example, a computer program product with a computer program that is directly loadable into the memory of a control unit of an MRI apparatus and includes program units to perform the acts of the method of one or more of the present embodiments when the program is executed by the control unit is provided. In addition to the computer program, such a computer program product may also include further parts such as documentation and/or additional components, also hardware components such as a hardware key (e.g., dongle, etc.) to facilitate access to the software.

A computer readable medium such as a memory stick, a hard-disk, or other transportable or permanently-installed carrier may serve to transport and/or to store the executable parts of the computer program product so that these may be read from a processor unit of an MRI apparatus. A processor unit may include one or more microprocessors or equivalents.

The method of one or more of the present embodiments may be applied in any appropriate MRI apparatus (e.g., in an MRI apparatus that has a superconducting magnet, a permanent magnet, or an electromagnet). However, a low-field MRI apparatus with a superconducting magnet benefits to a greater extent from the method of one or more of the present embodiments. In the following, therefore, but without restricting the present embodiments in any way, it may be assumed that the magnet of the MRI apparatus is a superconductive magnet.

It may also be assumed that the MRI apparatus is a low-field MRI apparatus. In one embodiment, the field strength of the magnet is at most 1.0 T, at most 0.7 T, at most 0.5 T, or at most 0.3. As indicated above, the RF bandwidth of a mid- or high-field MRI apparatus is generally large (e.g., body coil bandwidth ±100 kHz or more), but the bandwidth of a low-field apparatus is significantly narrower (e.g., as small as 10 kHz). In a further embodiment, the MRI apparatus has a body coil with a RF bandwidth that does not exceed 50 kHz.

An advantage of one or more of the present embodiments is that the target frequency of the magnet may be determined independently of an imaging sequence or MR-experiment (e.g., which would require the main magnetic field B0) and is determined solely based on reflection parameters of the body coil. In an embodiment, the magnet target frequency is determined in the absence of a main magnetic field. In other words, the magnet target frequency may be determined even when the main magnet has been ramped down. One or more of the present embodiments overcome a problem associated with low-field MRI systems (e.g., in such low-field systems, it is no longer practicable to specify the magnet frequency independently of the body coil frequency). In contrast to a high-field systems with a body coil bandwidth large enough to include a separately specified magnet frequency, the bandwidth of a low-field system is so narrow that the prior art approach of independently specifying the magnet frequency runs the risk of not lying within the body coil bandwidth.

To determine a suitable target frequency for the magnet in the next ramp event, the body coil center frequency is determined by measuring the reflection coefficients of the body coil as a function of frequency. A body coil excitation unit excites the body coil to emit an RF signal at a set or chosen frequency. According to one or more of the present embodiments, the center frequency of the body coil is deduced from a signal reflected by the body coil. The resonance curve of the reflected signal is detected and averaged in a suitable signal processing module to determine a corresponding center frequency. These computations may be performed in the frequency domain.

The resonance curve may be established by using a directional coupler to measure the reflectivity of the body coil. Such a directional coupler may already be a component of the MRI system. However, some simple MRI systems may not include such a directional coupler, or a directional coupler may be present but not equipped with the necessary detectors. Therefore, in a further embodiment, the center frequency of the reflected signal is determined by measuring the transmissivity between the body coil and a further coil of the MRI apparatus. This may be achieved in a relatively straightforward manner by using a wide-band transmit antenna to transmit a signal and by detecting the received signal. In one approach, this further coil may be a local coil of the MRI apparatus. Alternatively, the further coil may be a pickup coil of the MRI apparatus.

Once the body coil center frequency has been determined, the magnet target frequency may be computed. In an embodiment, the magnet target frequency is adjusted by adding an offset to the determined body coil center frequency.

As explained above, the first tolerance window has a different bandwidth than the second tolerance window. In a further embodiment, the first tolerance window is comparatively narrow and is applied when it is possible to precisely determine the magnet frequency. In one embodiment, the first tolerance window has a bandwidth of, for example, at most 5 kHz or at most 0.1 kHz. The first tolerance window may be applied when the magnet frequency may be estimated using a field probe, for example. By placing a field probe at a suitable position in the MRI apparatus (e.g., in the homogeneity volume or even into the isocenter of the B0 field), it is possible to establish a direct relationship between the current and/or voltage at the power supply and the detected echo frequency, thereby allowing the magnet frequency to be determined to a high degree of accuracy. The magnet may therefore be ramped to a target frequency near the upper boundary of the narrow tolerance window. Ramping to a higher target frequency will provide a longer duration (e.g., a wider decay window) before the magnet frequency decays to a lower limit.

In a further embodiment, the second tolerance window is comparatively wide and has a bandwidth of, for example, at most 50 kHz or at most 10 kHz. The second tolerance window therefore results in a lower target frequency. While this may appear to be a disadvantage, the advantage of being able to estimate the magnet frequency using a low accuracy shunt and performing a significantly shorter ramp procedure may outweigh the disadvantage of the shorter decay window.

The first tolerance window is used when the magnet is to be ramped to a high degree of precision using a field probe, for example. Alternatively, the first tolerance window is used when the magnet is to be ramped using an array shim device (e.g., a specific arrangement of field probes that is used during an initial installation procedure to establish a shim plot). This type of ramping procedure is more accurate but it takes a long time for the magnet to reach the higher first target frequency. Such ramping procedures generally require expertise and are performed by qualified personnel.

In one embodiment, the second target frequency is selected when the magnet is to be ramped in the absence of an MR echo frequency (e.g., without using a field probe or measuring a reflected signal from the body coil) or when the ramp procedure is to be performed without any user interaction. For example, a ramp procedure towards the second frequency may be performed using only the magnet power supply (MPSU) (e.g., by using an economical but inaccurate shunt to measure the current or voltage of the MPSU while ramping and estimating the momentary value of the magnet frequency to determine when the ramp sequence is complete). This less accurate ramping procedure takes a shorter time to reach the lower second target frequency and may be preferred when a user is not available to give user input, as may occur when the magnet is to be ramped autonomously. An example of such a scenario may be when the magnet is to be ramped up after a power or cooling outage that resulted in the magnet being ramped down, since power is required for the cooling system. When power returns and the cooling system is once again operating reliably, the magnet may be autonomously ramped up without requiring any user to be present.

The tolerance windows to be used for the different target frequencies may be predefined (e.g., defined by the manufacturer). The various parameters that define suitable tolerance windows may be supplied to the customer and may be stored in the system, or may be delivered with the system hardware, for example.

A target frequency is defined by the upper boundary of the body coil RF bandwidth and the appropriate tolerance window. This provides that the target frequency is always the highest possible for the next scheduled ramping event. This helps to increase the average interval between ramp events over the lifetime of the MRI system and to reduce the system downtime.

The upper boundary of the RF bandwidth may be either set as a fixed parameter or may be measured during tune-up or during a manufacturing stage. The upper boundary of the RF bandwidth may be stored in software, for example, as a system parameter. Alternatively, the upper boundary of the RF bandwidth may be an individual parameter that is specified with a major hardware component (e.g., the body coil) and is then read out from there by the central control system.

An advantage of one or more of the present embodiments is that either a first ramping mechanism or a second ramping mechanism may be selected based on user input, or the system may establish which of the two ramping mechanisms is most appropriate, depending on which hardware is connected to the system. For example, the presence of a shim array probe may be automatically recognized from a coil code that may be read by the MRI controller, which will then automatically select the narrower tolerance window. Ramp-up will be performed using field probes or the shim array device, and the reading of the MPSU sensor or shunt may be calibrated from the frequency measurement.

In one embodiment, during the ramp procedure, the magnet frequency is determined based on the magnet current as measured by a current sensor. The current sensor may include an ammeter shunt connected between the MPSU and the magnet. An ammeter shunt may measure large current values by a known and very small resistor in parallel with a moving coil galvanometer. Such an ammeter shunt is economical, with a significant inaccuracy when new (e.g., on the order of 500 ppm). The inaccuracy may increase even further to 5,000 ppm as a result of long-term aging effects. The magnet frequency may be derived from the current measured by the shunt. Owing to the relatively poor accuracy of the shunt, the measured magnet current may deviate from the magnet actual current by 500-5,000 ppm, so that the derived magnet frequency will deviate from the actual magnet frequency by 500-5,000 ppm. Even so, this rough estimation of the magnet frequency may allow a target frequency to be determined for a ramp procedure. Using such a rough estimate for the magnet current is a trade-off against the longer time it would take to ramp to a higher target frequency.

As an alternative to using a low-accuracy current sensor to estimate the magnet current and to derive the magnet frequency, the magnet frequency may be estimated based on a field measurement from a Hall sensor. Here also, the magnet frequency is derived in a comparatively inaccurate manner, since a Hall sensor may generally only measure the B0 field to within a limited accuracy, and the estimated field strength may differ by 500-50,000 ppm from the actual field strength.

In an embodiment, a center frequency is determined during an imaging procedure from signals received by the body coil or the local coils. These signals are essentially the signals originating from the patient during a clinical imaging sequence.

As indicated above, the main magnetic field will inevitably decay over time. While a system may be manufactured to a high degree of accuracy, and even though the magnet characteristics may be very precisely quantified, it is not feasible to predict exactly how a magnetic field will behave over several months or even years. However, it would be desirable for the customer (e.g., the radiology department of a clinic) to be informed of the status of the magnet at any time, so that routine maintenance events may be scheduled in a timely manner and so that down-time may be avoided.

In a method of one or more of the present embodiments, the recorded center frequencies may be stored in a memory module and/or may be forwarded to a remote service database for remote monitoring of the system. An alert or notification may be issued to the customer or user when the frequency approaches or transcends the limits of a predefined tolerance window.

The recorded center frequencies together with the maximum bandwidth and the decay-related characteristics make it possible to determine whether or not a center frequency is still within a predefined window, and/or to predict when the center frequency will leave the predefined window. A warning may be issued to the user or the customer service in good time (e.g., a few months or weeks ahead of the predicted time).

Therefore, in an embodiment, a decay-related characteristic includes a rate of decay of the main magnetic field. The customer or an online supervision system of a service IT infrastructure may compare this information with the magnet specification to see whether the rate of decay is in spec (e.g., the magnetic field is decaying as predicted by the manufacturer) or whether the rate of decay deviates from the predicted rate. Particularly in the case of a higher decay rate, it is advantageous to be aware of this so that corrective measures may be planned accordingly. In a further embodiment, a decay-related characteristic may be a decay level of the main magnetic field (e.g., the momentary percentage of the nominal field strength). The decay rate is effectively the rate of decay of the magnetic field (e.g., a first derivative $(dB/dt)$). Another decay characteristic that may be of interest is the rate of change of the decay rate (e.g., the second derivative $(d^2B/dt^2)$).

As explained above, a center frequency is obtained when a patient scan is being carried out. Occasionally, it may happen that patient scan is not performed entirely correctly (e.g., when a metallic object is within the homogeneity volume, when the door of the radio-frequency cabin is inadvertently left open, etc.), so that the measured center frequency is not actually representative. Therefore, in an embodiment, the method includes an act of filtering an identified center frequency prior to storing the identified center frequency. For example, a condition may be that an identified center frequency may not differ by more than ±50 ppm from a preceding center frequency. The filter is effectively a plausibility check that provides that outliers are not included in the record of center frequencies.

After subjecting an identified center frequency to the plausibility check, the identified center frequency is recorded in a memory. A representative center frequency value may be obtained by averaging the center frequencies (e.g., filtered center frequencies) measured during all patient scans during a specified time (e.g., during one day). The analysis unit may process a set of representative center frequencies to detect any decay of the main magnetic field. In one embodiment, the analysis unit processes, for example, at least two representative center frequencies or at least ten representative center frequencies to derive a decay characteristic of the main magnetic field. For example, one representative center frequency value may be obtained per day by averaging the center frequencies measured during all patient scans made that day, and the decay-related characteristic may be computed at the end of the week. Similarly, one representative center frequency value may be obtained from all patient scans made during one week, and the decay-related characteristic may be computed at the end of the month.

If a decay-related characteristic exceeds a predefined threshold (e.g., the magnet center frequency has dropped below a certain level) or the decay rate has increased beyond a certain acceptable rate, the operator of the MRI apparatus may be informed. Therefore, in an embodiment, the method includes issuing an alert when a decay-related characteristic exceeds a predefined threshold.

The method of one or more of the present embodiments may be used to advantage to observe the magnet field strength over time, and to plan any corrective measures such as a partial ramp or automatic ramp. For example, analysis of the center frequencies may indicate that the center frequency of the magnetic field has decayed to a level that may be remedied by carrying out a partial ramp-up procedure that may be carried out in the evening (e.g., when the MRI apparatus is not in use). A partial or "top-up" ramp may take only a relatively short period of time compared to a complete ramp-up procedure that requires the magnet to be ramped down completely and then ramped up again to reach the desired magnet field strength.

During ramp-up, current is fed to the magnet until the magnet current or the corresponding frequency has reached a predefined target current or frequency. The target frequency may be determined in any suitable manner (e.g., by arranging a probe inside the body coil and monitoring the magnet current using a current sensor of the magnet power supply). The MRI apparatus may include a probe placement device for automatically placing the probe inside the body coil.

In an embodiment, the MRI apparatus includes an ammeter shunt arranged to measure magnet current while ramping, so that the magnet frequency may be estimated. When the magnet frequency has been observed to reach the predefined target frequency, it may be assumed that the magnetic field is satisfactory and the ramp procedure may be concluded. An ammeter shunt is an economical but low-accuracy component and tends to become less accurate as the ammeter shunt ages. Therefore, in a further embodiment, the MRI apparatus includes a shunt monitoring module (e.g., the processor or another processor) configured to derive an aging characteristic of the current sensor based on patient scan center frequencies. A current measurement may be recorded at the end of a ramp-up sequence (e.g., when the magnet frequency has reached a target frequency). A calibration factor for the current sensor may be derived from a relationship between the shunt current measurement and a subsequent center frequency. The calibration factor may be expressed as a simple ratio (e.g., shunt current divided by center frequency).

In one embodiment, a shunt current measurement and a patient scan center frequency measurement are temporally close. Since the shunt current measurement may only be made during a ramp-up procedure, the center frequency measurement may be made during the patient scan following the ramp-up.

The calibration factor may be used to correct the current sensor readings during a subsequent ramp-up sequence, for example, and may significantly improve the accuracy of the ramp-up sequence, thereby extending the magnet field decay window. The calibration factor may also be used to correct for long-term aging effects of the shunt. The calibration factor may be used by the algorithms that deduce the magnet frequency from the current sensor measurements. In this way, the MRI apparatus may re-calibrate this functionality in a straightforward manner and prior to a next scheduled ramp-up procedure.

In a further embodiment, any acts of analyzing and evaluating the recorded center frequencies are performed remotely (e.g., on an external server). A remote customer support service may analyze the collected information and schedule a ramp-up event for MRI apparatus, so that the customer does not need to be concerned about these tasks.

BRIEF DESCRIPTION OF THE DRAWINGS

Other objects and features of the present invention will become apparent from the following detailed descriptions considered in conjunction with the accompanying drawings. It is to be understood, however, that the drawings are designed solely for the purposes of illustration and not as a definition of the limits of the invention.

DETAILED DESCRIPTION

In the diagrams, like numbers refer to like objects throughout. Objects in the diagrams are not necessarily drawn to scale.

Figure 1:
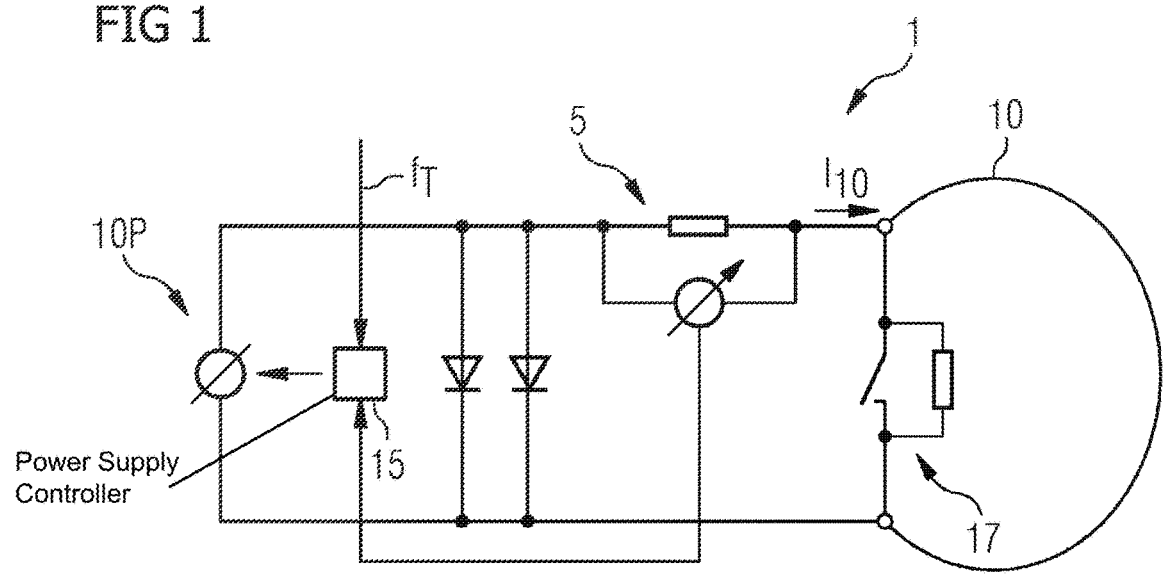
FIG. 1 shows a simplified circuit diagram of a superconductive low-field magnetic resonance imaging (MRI) apparatus according to an embodiment.

FIG. 1 shows a greatly simplified circuit diagram of one embodiment of a superconductive low-field MRI apparatus 1 (e.g., an MRI apparatus or an MRI system). The MRI apparatus 1 includes various modules and units, most of which will be known to the skilled person and need not be explained here. The MRI apparatus 1 includes a main magnet 10 that generates a very homogenous main magnetic field B0. An MPSU 10P is used to supply current $I_{10}$ to the magnet 10 during a ramp-up procedure when the magnet 10 is ramped to a previously determined target frequency. A switch assembly 17 including a superconducting switch in parallel with a bypass resistor is shown connected across the main magnet coil. The switch is closed during the ramp-up procedure so that a small amount of current passes through the bypass resistor. In this exemplary embodiment, an ammeter shunt S is used to measure the magnet current $I_{10}$ during ramping so that a power supply controller 15 may estimate the magnet frequency and compare the estimated magnet frequency to the target frequency $f_T$ so that the ramp-up procedure may be halted when the target frequency $f_T$ has been attained. At this point, the switch 17 is opened again.

Figure 2:
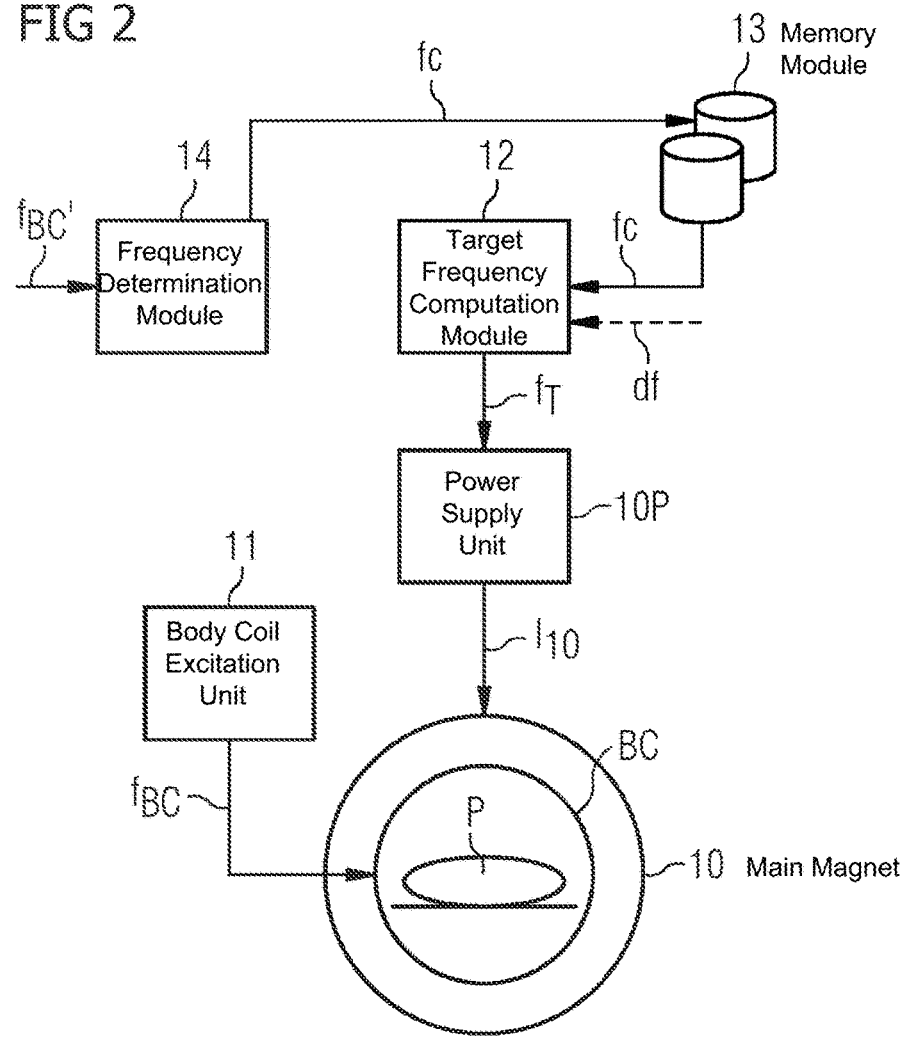
FIG. 2 shows a simplified block diagram of an MRI apparatus according to an embodiment.

FIG. 2 shows a simplified block diagram of one embodiment of the MRI apparatus 1 indicating the main magnet 10 and the body coil BC. The usual arrangement of additional coils such as shim coils, local coil, pickup coil, and a number of gradient coils may be assumed to be present. The diagram shows a body coil excitation unit 11 configured to excite the body coil BC to emit an RF signal at a chosen frequency $f_{BC}$. A reflected RF signal $f_{BC}'$ is detected, and a resonance curve of the reflected RF signal $f_{BC}'$ is analyzed in frequency determination module 14 (e.g., a processor) to identify a corresponding center frequency $f_c$. The center frequency $f_c$ is stored in a memory module 13 (e.g., a memory device) that may be realized as a memory module of the body coil BC, or as a memory module of a control unit (e.g., a controller, the processor, or another processor) of the MRI apparatus 1. The reflection coefficients of the system provide that the center frequency $f_c$ of the reflected body coil signal $f_{BC}'$ is lower than the body coil frequency $f_{BC}$.

A target frequency computation module 12 (e.g., the processor or another processor) determines a magnet target frequency $f_T$ based on the identified center frequency $f_c$. Depending on the type of ramp-up sequence that is to be carried out, an offset df may be added to the frequency $f_c$. In an exemplary process flow, the center frequency $f_c$ may be identified, for example, by the manufacturer or at some point during the lifetime of the MRI apparatus 1. Either way, the center frequency $f_c$ is stored in the memory module 13. Before carrying out a ramp-up sequence, the center frequency $f_c$ is retrieved from the memory module 13 and adjusted as necessary or as desired by a suitable offset df to give the target frequency $f_T$, and the magnet is ramped to the target frequency $f_T$.

A ramp control module is provided to initiate a subsequent ramping procedure at a suitable time. The magnet power supply unit 10P accordingly supplies current $I_{10}$ to the magnet 10 during the ramp-up procedure in order to ramp the main magnet 10 to that target frequency $f_T$.

The units and modules described above may be realized as part of a central control system of the MRI apparatus 1.

Figure 3:
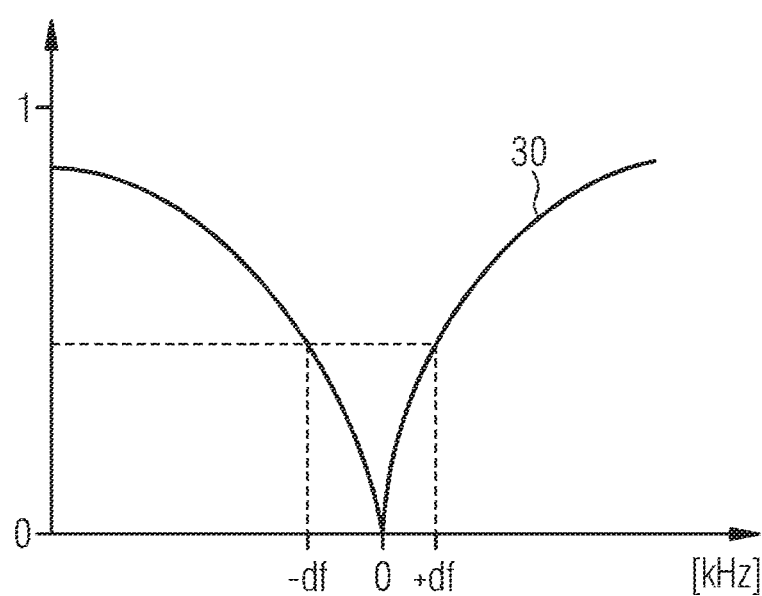
FIG. 3 illustrates a determination of a magnet target frequency using an embodiment of a method.

FIG. 3 shows an exemplary resonance curve of a body coil. The Y-axis shows reflection coefficients between 0 and 1. The X-axis shows frequency offset in kHz, with 0 corresponding to the minimum reflection coefficient. Such a curve is obtained by averaging the reflected body coil signal. The shape of the resonance curve 30 is determined largely by the Q-factor of the body coil. For the comparatively low magnet frequency of a low-field MRI system, the body coil has a high Q-factor during an imaging sequence (e.g., with a patient inside the body coil) on account of the low ohmic losses arising from lower conductivity. In a low-field MRI system, therefore, the quality of an imaging procedure is dependent on how well the magnet frequency and body coil frequency are matched. The lowest point or minimum of the resonance curve, corresponding to the center frequency $f_c$ of the reflected body coil signal, is identified and used to arrive at a magnet target frequency for a subsequent ramp-up sequence.

The target frequency may be set as the identified center frequency $f_c$ that was identified in the resonance curve of the body coil reflection. However, an offset may instead be added to the target frequency. The magnitude of the offset may be chosen based on the shape of the resonance curve and/or on various parameters of the ramp-up sequence. For example, by identifying a maximum reflection coefficient as indicated in FIG. 3, a resulting offset df may be identified. Generally, it is desired to set the magnet target frequency to be higher than the body coil frequency. Therefore, the target frequency $f_T$ may be expressed as:

$$f_T = f_c + df \qquad (1)$$

Alternatively, a fraction of the offset may be used (e.g., 25% of the offset). In this case, the target frequency $f_T$ may be expressed as $$f_T = f_c + \frac{df}{4} \qquad (2)$$

To give an example, the center frequency $f_c$ of the reflected signal may be determined to be 20.0 MHz. Adding a suitable offset such as 50 kHz, the target frequency $f_T$ for the next ramp event is determined to be 20.05 MHz using the above equation. In this way, the target frequency $f_T$ may be identified based on a desired accuracy of the intended ramping procedure. The method of one or more of the present embodiments of using an echo experiment to determine the magnet target frequency is associated with a favorably high degree of accuracy (e.g., with an error of less than 1.0 kHz). In another example, the center frequency $f_c$ of the reflected signal may be determined to be 30.1 MHz. Adding a suitable offset such as 10 kHz, the target frequency $f_T$ for the next ramp event is determined to be 30.11 MHz using the above equation.

Excitation of the body coil BC, measurement of the reflected body coil signal $f_{BC}'$, and computation of the center frequency $f_c$ and the target frequency $f_T$ may be performed entirely independently of the main magnet field B0, so that the method of one or more of the present embodiments may be carried out when the magnet 10 is ramped down.

Figure 4:
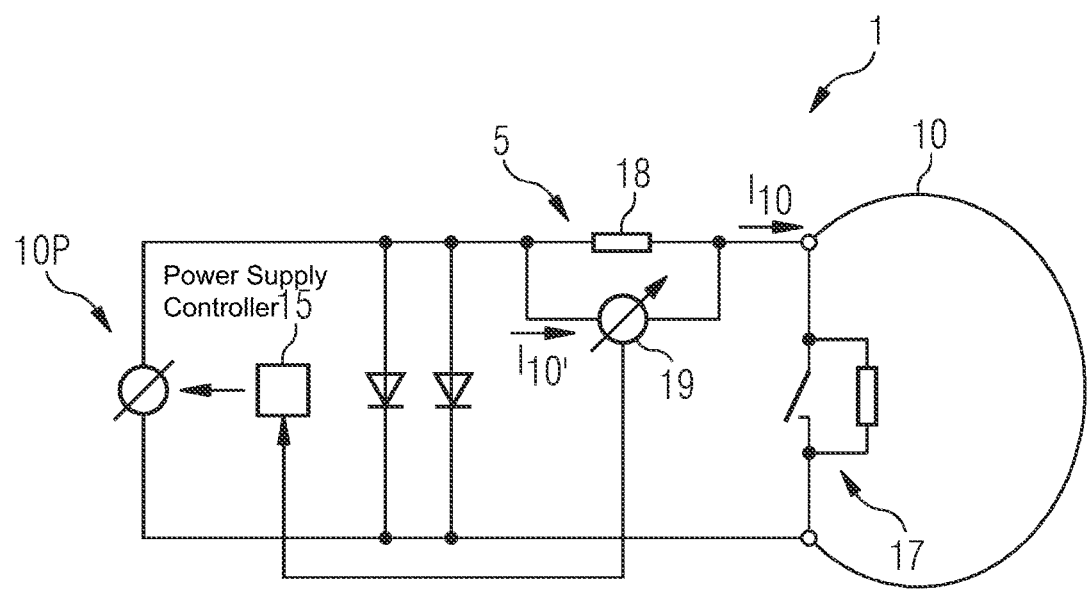
FIG. 4 shows a simplified circuit diagram of a superconductive low-field MRI apparatus according to an embodiment.
Figure 5:
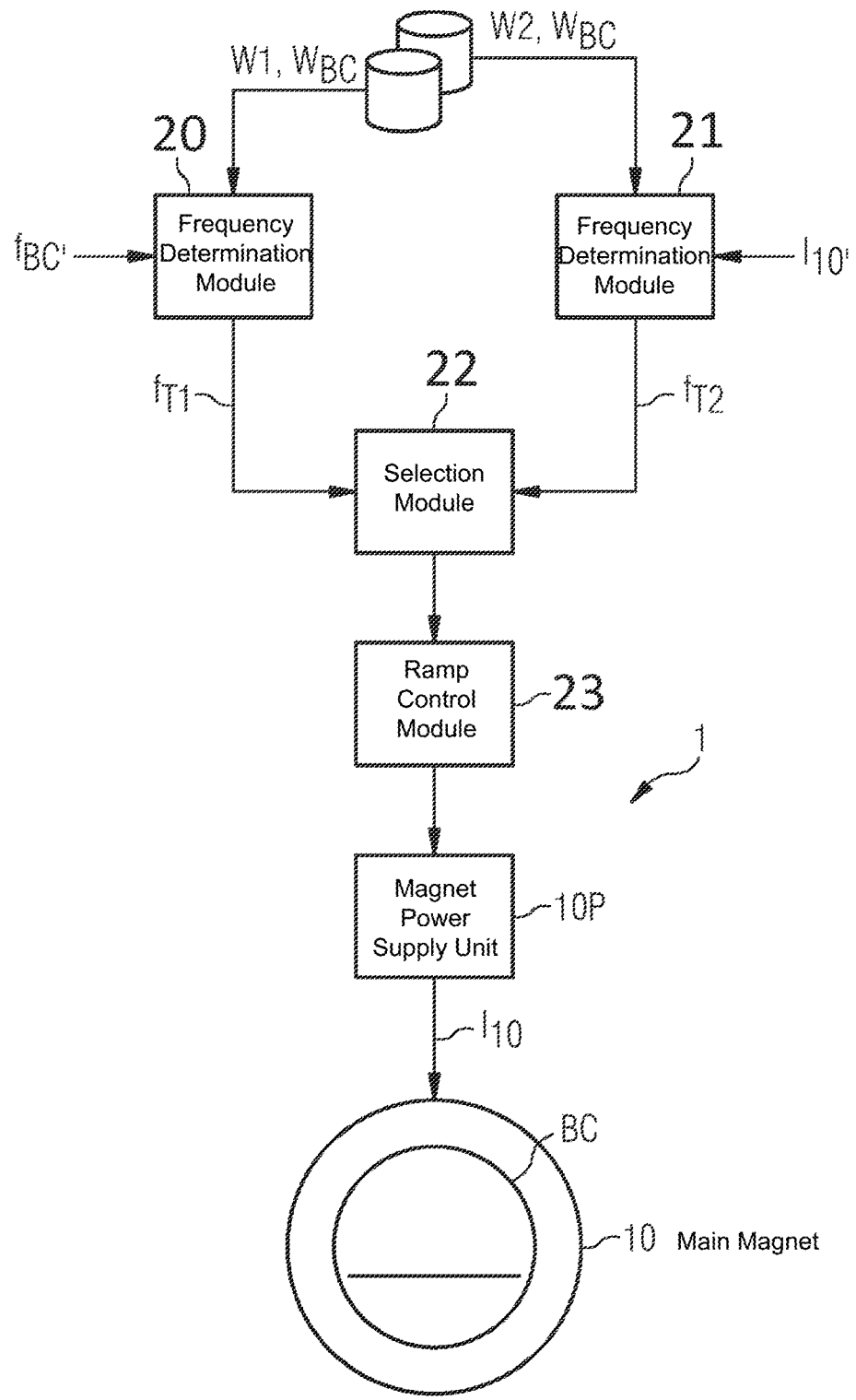
FIG. 5 shows a simplified block diagram of an MRI apparatus according to an embodiment.

FIG. 4 shows a greatly simplified circuit diagram of a superconductive low-field MRI apparatus 1. The MRI apparatus includes the main magnet 10 that generates a very homogenous main magnetic field B0. FIG. 5 shows a simplified block diagram of one embodiment of an MRI apparatus 1 indicating the main magnet 10. The usual arrangement of additional (e.g., a body coil BC, a shim coil, and a number of gradient coils) may be assumed to be present. An MPSU 10P is used to supply current $I_{10}$ to the magnet 10 during a ramp-up procedure. A switch assembly 17 including a superconducting switch in parallel with a bypass resistor is shown connected across the main magnet coil. The superconducting switch is closed during the ramp-up procedure so that a small amount of current passes through the bypass resistor. When the desired magnetic field strength has been reached, the switch is opened.

In this exemplary embodiment, a current sensor S is configured as an ammeter shunt and includes a shunt 18 and a galvanometer 19 arranged to measure current through the shunt 18. The measured current $I_{10}'$ corresponds essentially to the current $I_{10}$ through the magnet 10. Adjusting for the slight loss through the shunt, the magnet current $I_{10}$ may be determined to an accuracy of 500-5,000 ppm. The current sensor components will age over time, and this aging may be quantified and used to adjust the measured current value as appropriate.

The MRI system 1 may be delivered with a set of parameters such as a body coil RF bandwidth $W_{BC}$ and tolerance windows W1, W2 for use in computation of a target frequency. Any such parameters may be stored in a suitable memory module. FIG. 5 shows two frequency determination modules 20, 21, each of which is realized to identify a magnet target frequency $f_{T1}$, $f_{T2}$ based on a tolerance window W1, W2, a body coil RF bandwidth $W_{BC}$, and an appropriate input variable. To compute the higher first target frequency $f_{T1}$, the input variable to the first frequency determination module 20 is a measured RF signal $f_{BC}'$ reflected from the body coil BC when a probe is placed inside the body coil BC during ramp-up. To compute the lower second target frequency $f_{T2}$, the input variable to the second frequency determination module 21 is magnet current $I_{10}'$ measured by the ammeter shunt S.

A selection module 22 (e.g., the processor or another processor) is provided to select one of the computed magnet target frequencies $f_{T1}$, $f_{T2}$ as appropriate for the next re-ramp procedure. A ramp control module 23 (e.g., the processor or another processor) is provided to initiate a ramping procedure to ramp the main magnet 10 to the selected magnet target frequency $f_{T1}$, $f_{T2}$. The units and modules may be realized as part of a central control system of the MRI apparatus 1.

Figure 6:
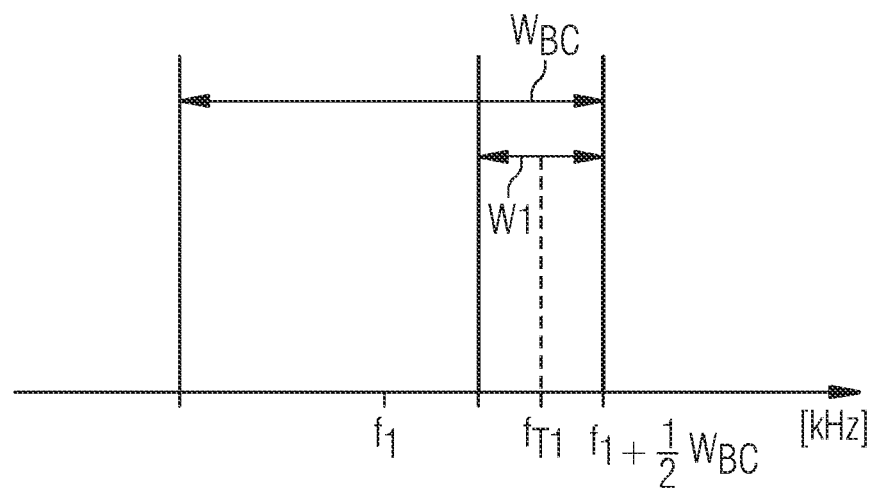
FIG. 6 illustrates an exemplary determination of a target frequency based on a narrow tolerance window.

FIG. 6 is a graph of amplitude against frequency, illustrating the computation of a target frequency $f_{T1}$ for a ramping procedure, based on a narrow tolerance window W1. In this case, the upper boundary of the body coil radio-frequency bandwidth $W_{BC}$ may be either set as a fixed parameter or may be measured during a tuning procedure or during a manufacturing stage. For example, the body coil RF bandwidth $W_{BC}$ may be in the order of 50 kHz. This information may be stored in software as a system parameter or may be a parameter that is delivered with the body coil (e.g., in a memory such as an EEPROM or a flash memory that is part of the body coil system). The body coil RF bandwidth $W_{BC}$ may be read out from such a memory module by a controller of the MRI apparatus.

In this comparatively accurate method, a probe is placed in the body coil BC, and the magnet frequency $f_1$ is calculated.

The first target frequency $f_{T1}$ may then be expressed as $$f_{T1} = f_1 + \tfrac{1}{2}W_{BC} - \tfrac{1}{2}W1 \qquad (3)$$

To give an example, the frequency $f_1$ of the magnet may be estimated using a probe to be about 20 MHz. Using a known body coil RF bandwidth $W_{BC}$ of 30 kHz and the known narrow window W1 of 1 kHz, the target frequency $f_{T1}$ for the next ramp event is determined to be 20.014500 MHz using equation (3).

Figure 7:
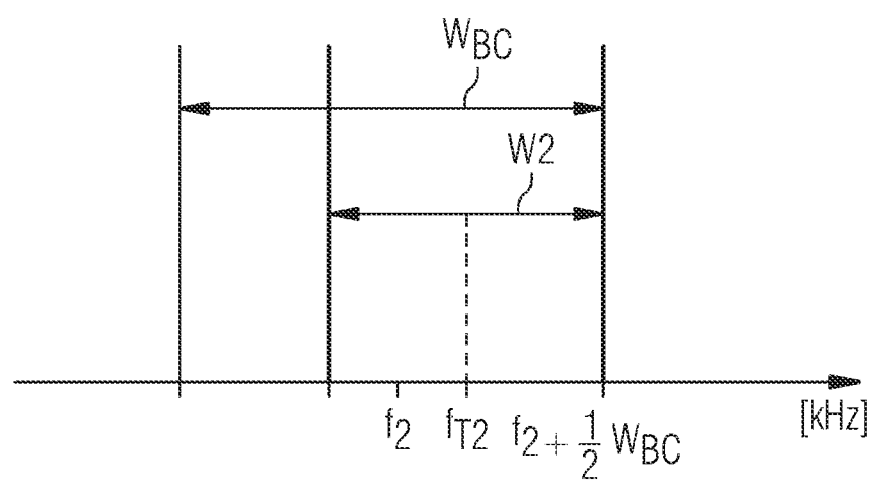
FIG. 7 illustrates an exemplary determination of a target frequency based on a wide tolerance window.

FIG. 7 is a graph of amplitude against frequency, illustrating the computation of a second target frequency $f_{T2}$ for a ramping procedure, based on a wide tolerance window W2. The upper boundary of the radio-frequency bandwidth $W_{BC}$ is known, as explained in FIG. 6 above. The wide tolerance window W2 is also known. The magnet frequency $f_2$ is estimated using the comparatively inaccurate current $I_{10}'$ measured using the shunt S of FIG. 4.

The second target frequency $f_{T2}$ may then be expressed as $$f_{T2} = f_2 + \tfrac{1}{2}W_B - \tfrac{1}{2}W2 \qquad (4)$$

To give an example, the frequency $f_2$ of the magnet may be estimated using the shunt to be about 20 MHz. Using a known body coil RF bandwidth $W_{BC}$ of 30 kHz and the known wide window W2 of 10 kHz, the target frequency $f_{T2}$ for the next ramp event is determined to be 20.01 MHz using equation (4).

This roughly computed target frequency $f_{T2}$ may be used when an autonomous ramp-up sequence is to be performed or when there is no user available to place a field probe, for example.

Figure 8:
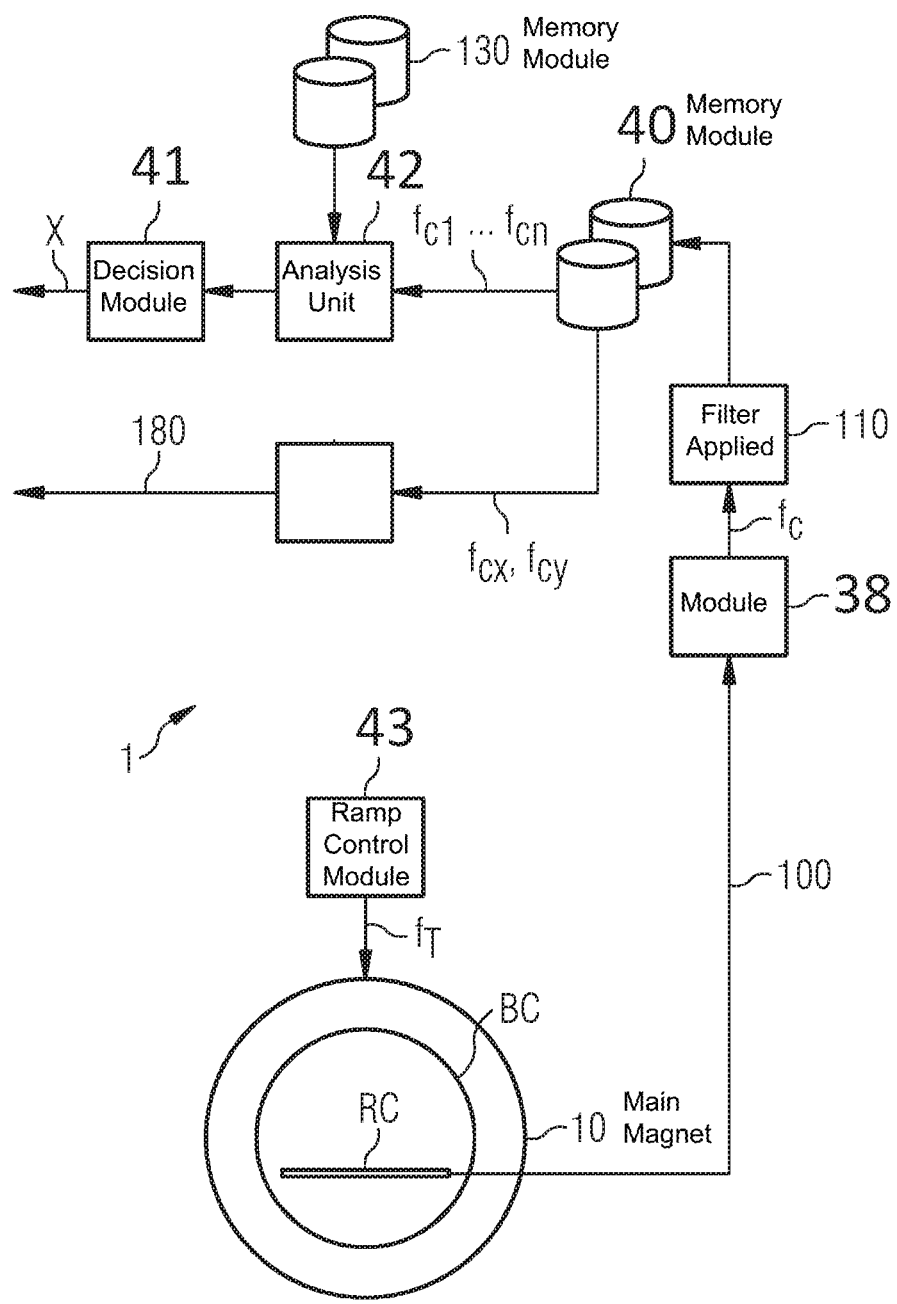
FIG. 8 shows a simplified block diagram of an MRI apparatus according to an embodiment.

One embodiment of the MRI apparatus 1 includes a main magnet that generates a very homogenous main magnetic field B0. FIG. 8 shows a simplified block diagram of one embodiment of the MRI apparatus 1 indicating the main magnet 10, the body coil BC, and a receiver coil RC (e.g., a flat receive-only spine coil). The usual arrangement of additional coils such as shim coils, local coil, pickup coil and a number of gradient coils may be assumed to be present. During a patient scan, the body coil BC is excited to emit an RF signal, and the receiver coil RC detects a reflected RF signal 100. The reflected RF signal 100 is processed by a module 38 (e.g., the processor or another processor) that performs appropriate signal processing steps to identify the center frequency $f_c$ of the received signal 100. To exclude any outliers, a filter is applied in block 110, which may compare the present center frequency $f_c$ to the previous center frequency. The present center frequency $f_c$ is only approved if, for example, the present center frequency $f_c$ does not differ from a predecessor by more than ±50 ppm. If approved, the present center frequency $f_c$ is then stored in a memory module 40 (e.g., a memory device). These steps are repeated for successive patient scans, so that ultimately, a collection of center frequencies accumulates in the memory module 40.

The frequency of a received RC signal is related to the magnetic field strength by the relationship $$f = \frac{\gamma}{2\pi} B0 \qquad (5)$$

where $\gamma$ is the gyromagnetic ratio. An analysis module (e.g., the processor or another processor) processes a plurality of the successively collected center frequencies $f_{c1}, \ldots, f_{c1}$ to identify a trend. For example, a gradual shift in frequency indicates a gradual decay of the main magnetic field. The analysis module may compare an identified decay trend with an expected decay trend known from the magnet specification, stored, for example, in a memory module 130 (e.g., a memory device). A decision module 41 (e.g., the processor or another processor) may determine whether action is to be taken based on the information provided by the analysis unit 42 (e.g., the processor or another processor). For example, the decision module may issue an alert X if a field strength decay rate is observed to be faster than an expected or specified decay rate.

Figure 9:
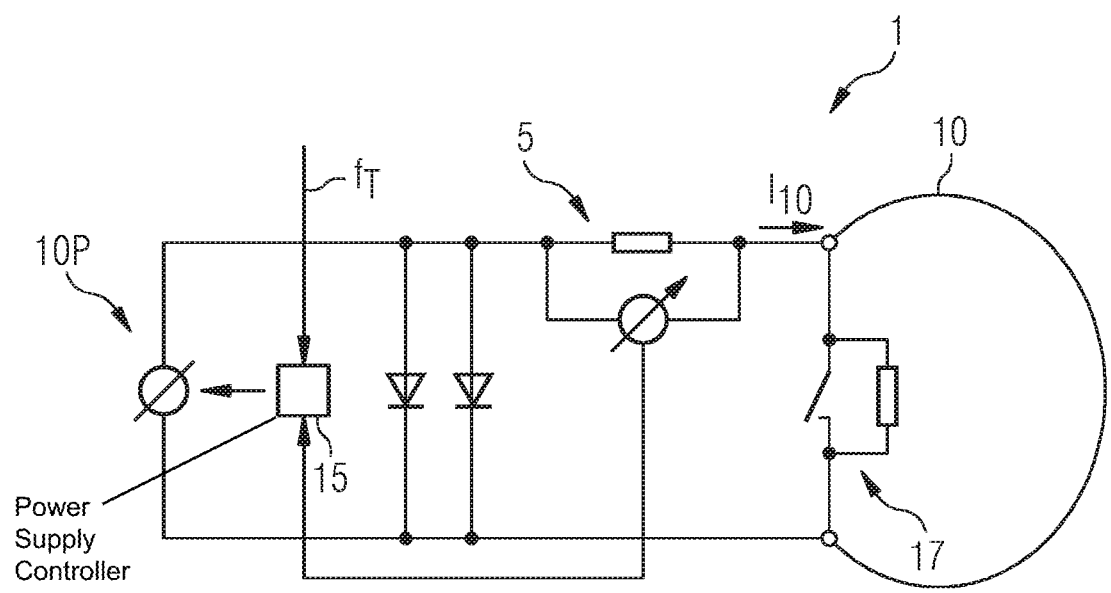
FIG. 9 shows a simplified circuit diagram of a superconductive low-field MRI apparatus according to an embodiment.

A ramp control module 43 (e.g., the processor or another processor) is provided to initiate a ramping procedure at a suitable time in order to ramp the main magnet 10 to a target frequency $f_T$. FIG. 9 shows a greatly simplified circuit diagram of an embodiment of such a superconductive low-field MRI apparatus 1. An MPSU 10P is used to supply current $I_{10}$ to the magnet 10 during a ramp-up procedure, when the magnet 10 is ramped to the previously determined target frequency. A switch assembly 17 including a superconducting switch in parallel with a bypass resistor is shown connected across the main magnet coil 10. The switch is closed during the ramp-up procedure so that a small amount of current passes through the bypass resistor. In this exemplary embodiment, an ammeter shunt S is used to measure the magnet current $I_{10}$ during ramping so that a power supply controller 15 may estimate the magnet frequency and compare the estimated magnet frequency to the target frequency $f_T$ so that the ramp-up procedure may be halted when the target frequency $f_T$ has been attained. At this point, the switch 17 is opened again.

Returning to FIG. 9, a current measurement may be recorded at the end of a ramp-up sequence (e.g., when the magnet frequency has reached a target frequency). A calibration factor for the current sensor may be derived from a relationship between the current measurement and a subsequent center frequency. A calibration factor C may be expressed as a simple ratio of shunt current to center frequency, such as, for example $$C = \frac{I_{10}}{f_c} \quad (6)$$

The shunt current measurement and a patient scan center frequency measurement may be temporally close. Since the shunt current measurement may only be made during a ramp-up procedure, the center frequency measurement may be made during the patient scan following the ramp-up.

The calibration factor C may be used in a subsequent ramp-up procedure to correct for aging effects of the shunt S. The calibration factor C may be forwarded to the controller 15 of the MPSU 10P, for example, so that subsequent current readings may be corrected, and the ramp-up procedure may be performed to a higher degree of accuracy.

The units and modules described above may be realized as part of a central control system of the MRI apparatus 1.

Figure 10:
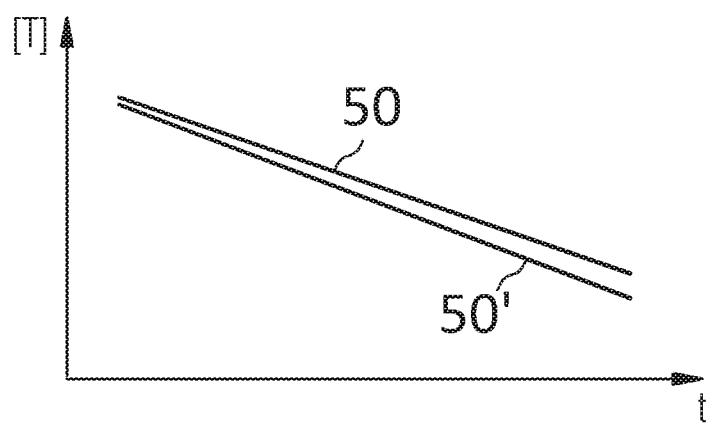
FIG. 10 shows an exemplary graph of magnet field decay obtained using an embodiment.

FIG. 10 is a graph of magnet field decay showing magnet field strength (in Tesla) against time (in a timescale of months or even years). The diagram shows an expected decay profile 50 and a deduced decay profile 50' that is established by analyzing a series of patient scan center frequencies. In this exemplary case, the decay profile 50' shows a faster rate of decay than the expected decay profile 50 and may result in a decision to carry out a re-ramp event sooner than originally scheduled.

Figure 11:
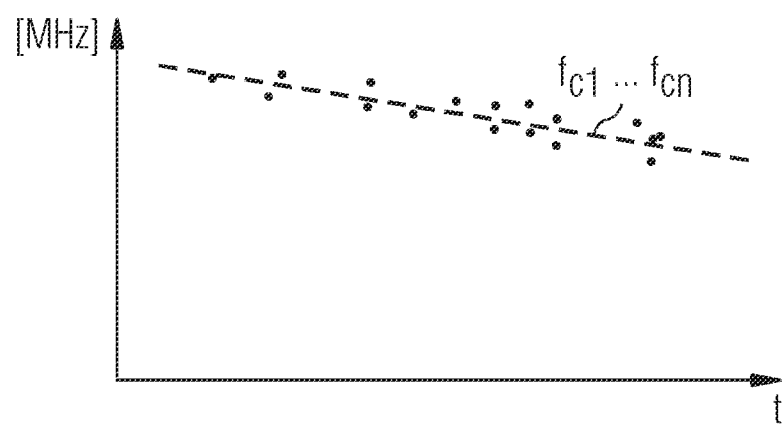
FIG. 11 shows a first graph of exemplary patient scan center frequencies obtained using an embodiment of a method.

FIG. 11 indicates how a collection of patient scan center frequencies may be used to establish a magnet field decay characteristic. The identified center frequencies $f_{c1}, \ldots, f_{cn}$ are indicated by dots. The graph shows frequency on the X-axis (in MHz) against scan count along the Y-axis. The diagram shows a gradual decrease in the center frequencies $f_{c1}, \ldots, f_{cn}$ of the detected RC signal. Using an appropriate interpolation or best-fit technique, the frequencies may be translated into a decay profile 50' of the main magnetic field as shown in FIG. 10.

Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements. The mention of a "unit" or a "module" does not preclude the use of more than one unit or module.

The invention claimed is:

1. A method of operating a magnetic resonance imaging (MRI) apparatus, the method comprising:
    identifying a center frequency during an imaging procedure and recording center frequencies of a magnet identified in successive imaging procedures;
    identifying, by a processor, a number of decay-related characteristics of a main magnetic field of the MRI apparatus, the identifying of the number of decay-related characteristics of the main magnetic field comprising analyzing the center frequencies, the main magnetic field being a static B0 field; and
    adapting a schedule for re-ramping the magnet based on a decay-related characteristic of the number of decay-related characteristics,
    wherein analyzing the center frequencies comprises averaging a plurality of center frequencies measured during patient scans during a specified interval.

2. A magnetic resonance imaging (MRI) apparatus comprising:
    a center frequency identifier module configured to identify a center frequency during an imaging procedure;
    a storage device configured to record center frequencies of a magnet identified during successive imaging procedures; and
    a processor configured to:
        identify a number of decay-related characteristics of a main magnetic field from analysis of the recorded center frequencies, the main magnetic field being a static B0 field; and
        adapt a schedule for re-ramping the magnet based on a decay-related characteristic of the number of decay-related characteristics,
    wherein the analysis of the recorded center frequencies comprises an average of a plurality of center frequencies measured during patient scans during a specified interval.

3. In a non-transitory computer-readable storage medium that stores instructions executable by one or more processors to operate a magnetic resonance imaging (MRI) apparatus, the instructions comprising:
    identifying a center frequency during an imaging procedure and recording center frequencies of a magnet identified in successive imaging procedures;
    identifying, by the one or more processors, a number of decay-related characteristics of a main magnetic field of the MRI apparatus, the identifying of the number of decay-related characteristics of the main magnetic field comprising analyzing the center frequencies, the main magnetic field being a static B0 field;

deriving an aging characteristic of a current sensor from a current measurement obtained during a ramp-up sequence and a center frequency identified after the ramp-up sequence; and adapting a schedule for re-ramping the magnet based on a decay-related characteristic of the number of decay-related characteristics.

4. A method of operating a magnetic resonance imaging (MRI) apparatus, the method comprising:

identifying a center frequency during an imaging procedure and recording center frequencies of a magnet identified in successive imaging procedures;

filtering prior to storing the identified center frequency;

identifying, by a processor, a number of decay-related characteristics of a main magnetic field of the MRI apparatus, the identifying of the number of decay-related characteristics of the main magnetic field comprising analyzing the center frequencies, the main magnetic field being a static B0 field; and adapting a schedule for re-ramping the magnet based on a decay-related characteristic of the number of decay-related characteristics.

5. The method of claim 1, wherein a decay-related characteristic of the number of decay-related characteristics comprises a rate of decay of the main magnetic field.

6. The method of claim 1, further comprising filtering prior to storing the identified center frequency.

7. The method of claim 1, further comprising issuing an alert when a decay-related characteristic of the number of decay-related characteristics exceeds a predefined threshold.

8. The method of claim 1, further comprising deriving an aging characteristic of a current sensor from a current measurement obtained during a ramp-up sequence and a center frequency identified after that ramp-up sequence.

9. The method of claim 1, wherein analyzing the center frequencies is performed at a remote location from the MRI apparatus.

10. The MRI apparatus of claim 2, further comprising:
an ammeter shunt arranged to measure magnet current during a ramp procedure; and
a shunt monitoring module configured to derive an aging characteristic of the ammeter shunt based on consecutive identified center frequencies.

11. The MRI apparatus of claim 2, wherein a field strength of the magnet of the MRI apparatus is at most 1.0 Tesla.

12. The non-transitory computer-readable storage medium of claim 3, wherein analyzing the center frequencies comprises averaging a plurality of center frequencies measured during patient scans during a specified interval.

13. The non-transitory computer-readable storage medium of claim 3, wherein a decay-related characteristic of the number of decay-related characteristics comprises a rate of decay of the main magnetic field.

14. The non-transitory computer-readable storage medium of claim 13, wherein a decay-related characteristic of the number of decay-related characteristics comprises a rate of change of the rate of decay of the main magnetic field.

15. The non-transitory computer-readable storage medium of claim 3, wherein the instructions further comprise filtering prior to storing the identified center frequency.

16. The non-transitory computer-readable storage medium of claim 3, wherein the instructions further comprise issuing an alert when a decay-related characteristic of the number of decay-related characteristics exceeds a predefined threshold.

17. The non-transitory computer-readable storage medium of claim 3, wherein analyzing the center frequencies is performed at a remote location from the MRI apparatus.

18. The method of claim 5, wherein a decay-related characteristic of the number of decay-related characteristics comprises a rate of change of the rate of decay of the main magnetic field.

19. The MRI apparatus of claim 11, wherein the magnet is a superconductive magnet.

* * * * *

UNITED STATES PATENT AND TRADEMARK OFFICE
CERTIFICATE OF CORRECTION

PATENT NO. : 12,105,168 B2
APPLICATION NO. : 17/882526
DATED : October 1, 2024
INVENTOR(S) : Stephan Biber et al.

Page 1 of 1

It is certified that error appears in the above-identified patent and that said Letters Patent is hereby corrected as shown below:

On the Title Page

Add item (30) Foreign Application Priority Data:
"Aug. 21, 2018 (EP) ................................ 18189964
Aug. 21, 2018 (EP) ................................ 18189973
Aug. 21, 2018 (EP) ................................ 18189940"

Signed and Sealed this
Fourth Day of March, 2025

Coke Morgan Stewart
*Acting Director of the United States Patent and Trademark Office*